(12) United States Patent
Chamchoum

(10) Patent No.: US 11,937,683 B2
(45) Date of Patent: Mar. 26, 2024

(54) FROZEN SKIN SERUM AND APPLICATOR THEREOF

(71) Applicant: Christina Chamchoum, Los Angeles, CA (US)

(72) Inventor: Christina Chamchoum, Los Angeles, CA (US)

( * ) Notice: Subject to any disclaimer, the term of this patent is extended or adjusted under 35 U.S.C. 154(b) by 306 days.

(21) Appl. No.: 17/306,794

(22) Filed: May 3, 2021

(65) Prior Publication Data

US 2022/0346530 A1  Nov. 3, 2022

(51) Int. Cl.
| | |
|---|---|
| *A45D 40/26* | (2006.01) |
| *A61K 8/02* | (2006.01) |
| *A61K 8/34* | (2006.01) |
| *A61K 8/67* | (2006.01) |
| *A61K 8/73* | (2006.01) |
| *A61K 8/9789* | (2017.01) |
| *A61K 8/9794* | (2017.01) |
| *A61Q 19/00* | (2006.01) |

(52) U.S. Cl.
CPC .......... *A45D 40/261* (2013.01); *A61K 8/0216* (2013.01); *A61K 8/342* (2013.01); *A61K 8/676* (2013.01); *A61K 8/735* (2013.01); *A61K 8/9789* (2017.08); *A61K 8/9794* (2017.08); *A61Q 19/00* (2013.01); *A61K 2800/874* (2013.01)

(58) Field of Classification Search
CPC ...... A45D 40/261; A61K 8/735; A61K 8/676; A61K 8/9798; A61K 8/9794; A61K 8/342; A61K 2800/874; A61Q 19/00
USPC ......................................... 401/209, 215, 219
See application file for complete search history.

(56) References Cited

U.S. PATENT DOCUMENTS

| | | | | |
|---|---|---|---|---|
| 4,886,168 A | * | 12/1989 | Bontemps | A61K 8/982 206/823 |
| 10,758,024 B2 | * | 9/2020 | Corbellini | A45D 33/26 |
| 2022/0304449 A1 | * | 9/2022 | Truong | A45D 40/265 |

\* cited by examiner

*Primary Examiner* — David J Walczak
(74) *Attorney, Agent, or Firm* — The Rapacke Law Group, P.A.; Andrew S. Rapacke

(57) ABSTRACT

A frozen serum and applicator thereof, including a mold having a first half releasably engaged with a second half. When engaged, the first half and the second half form a reservoir therebetween to accept a volume of serum. The serum is frozen within the mold to produce a frozen serum having at least one receiver molded thereon to releasably engage with an applicator configured to permit the frozen serum to be rolled. An opening is provided on the mold to permit the serum to be disposed within the reservoir.

15 Claims, 3 Drawing Sheets

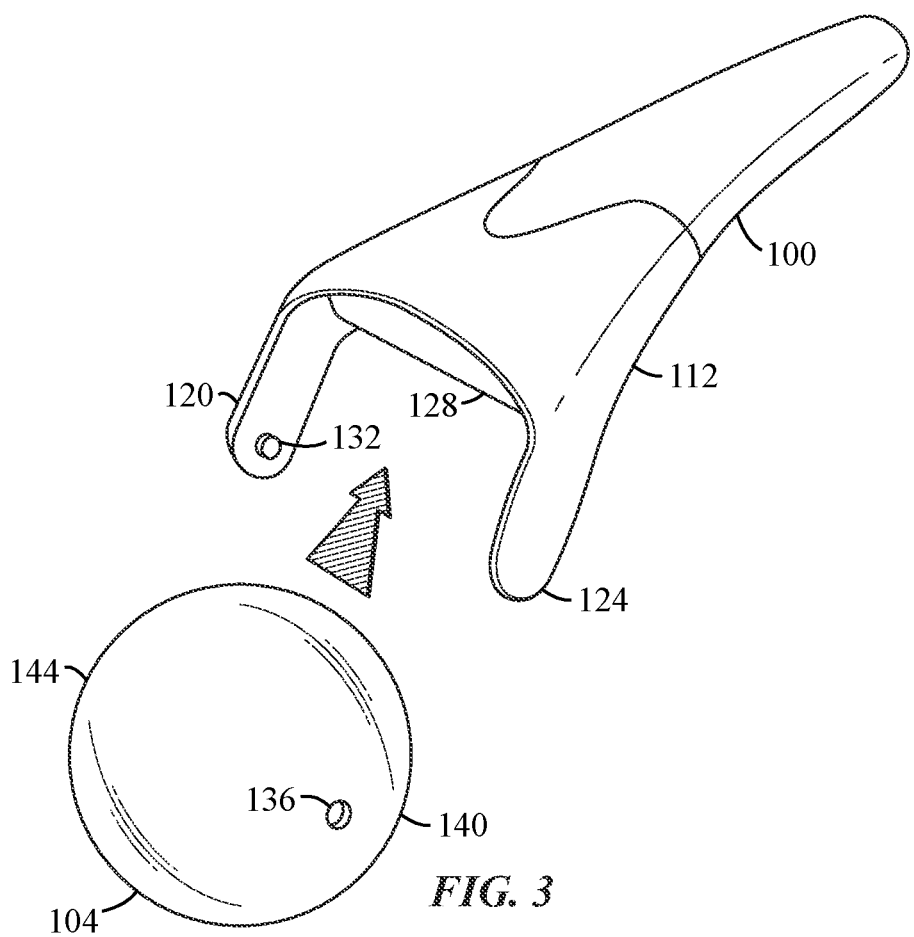
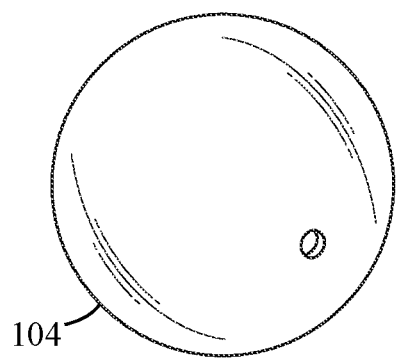
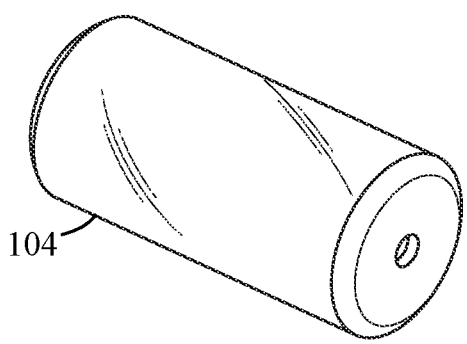
FIG. 3
FIG. 4
FIG. 5

FROZEN SKIN SERUM AND APPLICATOR THEREOF

TECHNICAL FIELD

Embodiments of the invention relate to skincare products and more particularly relate to frozen skin serums and applicators thereof.

BACKGROUND

Cosmetic packaging often includes an applicator that is suitable for dispensing the particular cosmetic. Skincare products may include a cream, serum, or other liquid, gel, emulsion, etc. which is spread onto the skin using the applicator. In some instances, the applicator may function to massage the skin at the application site. It is believed that cooling the skin may have various benefits, such as by reducing inflammation associated with puffiness. For example, many believe that cooling the skin below the eyes will reduce eye puffiness.

In the current arts, rollers are pre-chilled to cool the roller surface which can be applied to the skin. Similarly, some will cool cosmetics prior to applying the cosmetic. However, this results in a limited cooling effect as the cosmetic quickly raises temperature upon contact with the skin.

SUMMARY OF THE INVENTION

This summary is provided to introduce a variety of concepts in a simplified form that is disclosed further in the detailed description of the embodiments. This summary is not intended to identify key or essential inventive concepts of the claimed subject matter, nor is it intended for determining the scope of the claimed subject matter.

The embodiments provided herein relate to a frozen serum and applicator thereof, including a mold having a first half releasably engaged with a second half. When engaged, the first half and the second half form a reservoir therebetween to accept a volume of a serum. The serum is frozen within the mold to produce a frozen serum having at least one receiver molded thereon to releasable engage with an applicator configured to permit the frozen serum to be rolled. An opening is provided on the mold to permit the serum to be disposed within the reservoir.

The skin serum is disposed within a mold and frozen prior to use. The mold is designed to retain the serum within the mold while freezing while shaping the serum into a configuration compatible with the applicator such that the frozen serum may be removed from the mold and releasably engaged with the applicator.

In one aspect, the serum is comprised of at least one of the following: hyaluronic acid, vitamin C, jojoba oil, aloe vera, and retino.

In one aspect, the serum has a freezing temperature of about 0° Celsius.

In one aspect, the applicator includes a handle portion positioned at a first end of the applicator.

In one aspect, the applicator includes a receiver portion positioned at the second end of the applicator.

In one aspect, the receiver portion includes a first arm and a second arm.

In one aspect, the first arm and the second arm each include a protrusion to interface with the at least one receiver on the frozen serum to permit the frozen serum to be rolled.

In one aspect, the first arm and the second arm are flexible.

In one aspect, the frozen serum is shaped as a sphere or as a cylinder.

In one aspect, the handle portion releasably engages with the receiver portion.

In one aspect, the frozen serum is melted and reused in future applications.

BRIEF DESCRIPTION OF THE DRAWINGS

A more complete understanding of the embodiments, and the attendant advantages and features thereof, will be more readily understood by references to the following detailed description when considered in conjunction with the accompanying drawings wherein:

FIG. 3 illustrates an exploded view of the applicator having the frozen serum removed from the applicator, according to some embodiments;

FIG. 4 illustrates a perspective view of the frozen serum shaped as a sphere, according to some embodiments;

FIG. 5 illustrates a perspective view of the frozen serum shaped as a cylinder, according to some embodiments.

DETAILED DESCRIPTION

Figure 1:
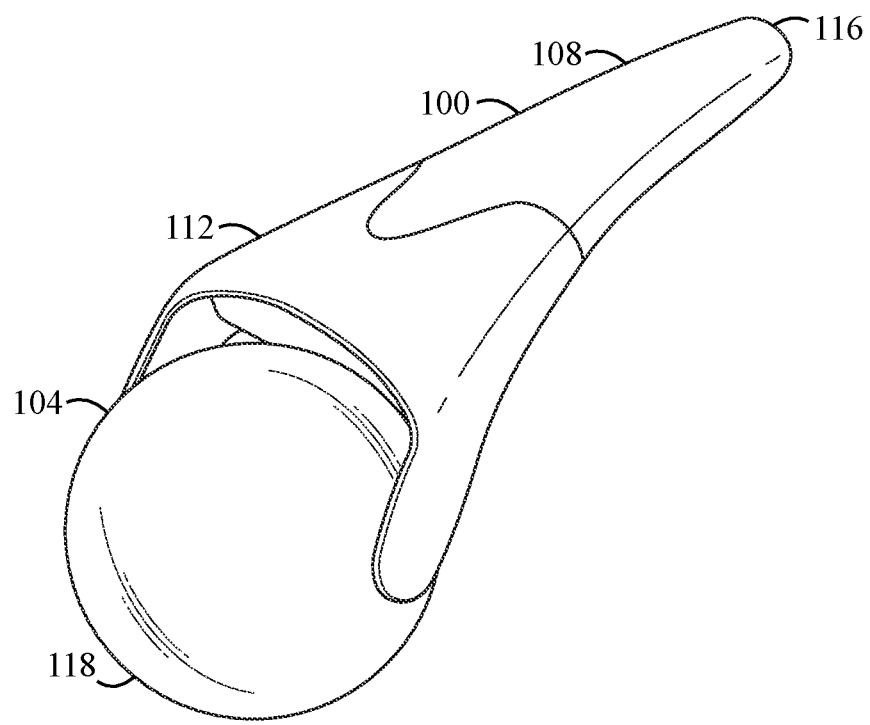
FIG. 1 illustrates a perspective view of the applicator and frozen serum, according to some embodiments.

The specific details of the single embodiment or variety of embodiments described herein are set forth in this application. Any specific details of the embodiments are used for demonstration purposes only, and no unnecessary limitation or inferences are to be understood therefrom.

Before describing in detail exemplary embodiments, it is noted that the embodiments reside primarily in combinations of components related to the system. Accordingly, the device components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

In general, the embodiments described herein relate to a frozen skin serum and applicator thereof. The skin serum is disposed within a mold and frozen prior to use. The mold is designed to retain the serum within the mold while freezing while shaping the serum into a configuration compatible with the applicator such that the frozen serum may be removed from the mold and releasably engaged with the applicator.

Figure 2:
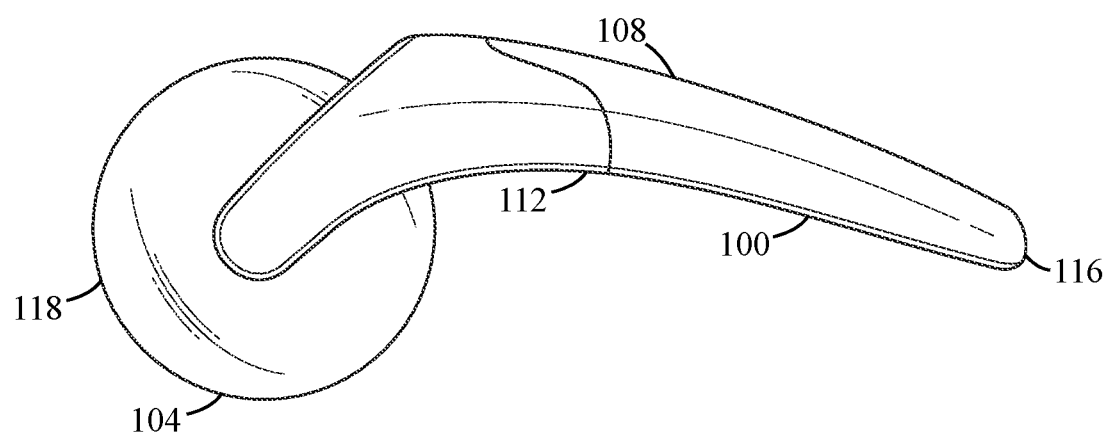
FIG. 2 illustrates a side elevation view of the applicator and frozen serum, according to some embodiments.

FIG. 1 and FIG. 2 illustrate the applicator 100 and frozen serum 104. The applicator 100 includes a handle portion 108 to permit the user to hold the applicator 100 while applying the frozen serum 104 onto their skin. The handle portion 108 extends to a receiver portion 112 configured to releasable engage with the frozen serum 104. The handle portion 108 is positioned at a first end 116 of the applicator 100 and the frozen serum 104 is positioned at the second end 118 of the application 100. The handle portion 108 may be ergonomically shaped to provide a comfortable interface between the handle and the user's hand. Further, the handle portion 108 allows the user to apply pressure when rolling and applying the frozen serum 104 onto the skin.

In some embodiments, the handle portion 108 is integrally molded to the receiver portion 112. Alternatively, the handle portion 108 may be releasable engaged with the receiver portion 112 to permit the user to interchange receiving portion which accommodate various sizes, shapes, and configurations of frozen serums 104.

FIG. 3 illustrates an exploded view of the applicator 100 having the frozen serum 104 removed from the receiver portion 112. The receiver portion 112 include a first arm 120 and a second arm 124 separated by a central portion 128. The frozen serum 104 is dimensioned such that the first arm 120 and second arm 124 at least partially contact the edge of the frozen serum 104 and allow the frozen serum 104 to rotate when being applied to the skin. Each arm 120, 124 includes a protrusion 132 to releasably engage with a receiver 136 on each side 140,144 of the frozen serum 104. In such, the frozen serum 104 is retained on the applicator 100 throughout use and during storage when not in use.

In some embodiments, the first and second arms 120, 124 are constructed of a flexible material such that the first and second arms 120, 124 can bend to accommodate frozen serums 104 of various sizes, shapes, and configuration. This may be especially useful as the frozen serum 104 melts during use.

FIG. 4 and FIG. 5 illustrate the frozen serum 104 in a spherical (see FIG. 4) and cylindrical (see FIG. 4) configuration. One skilled in the arts will readily understand that the size, shape, and configuration may be changed based on user preference, or particular applicator shape and size. Further, while shapes which can roll (e.g., spheres, cylinders, ovoids, etc.) may be most convenient for the user to promote even melting of the frozen serum 104, the shape may be other shapes including cubes. The frozen serum 104 may be formulated from various skincare ingredients known in the arts, and especially from compositions which freeze at 0° Celsius. For example, the frozen serum can include hyaluronic acid, vitamin C, jojoba oil, aloe vera, retino, and combinations thereof. The composition may include various surfactants, thickening agents, solids (including soluble and insoluble solids), fragrances, colorants, and the like which may provide the desired effect, treatment, aesthetic appearance, and scent to the frozen serum composition.

Figure 6:
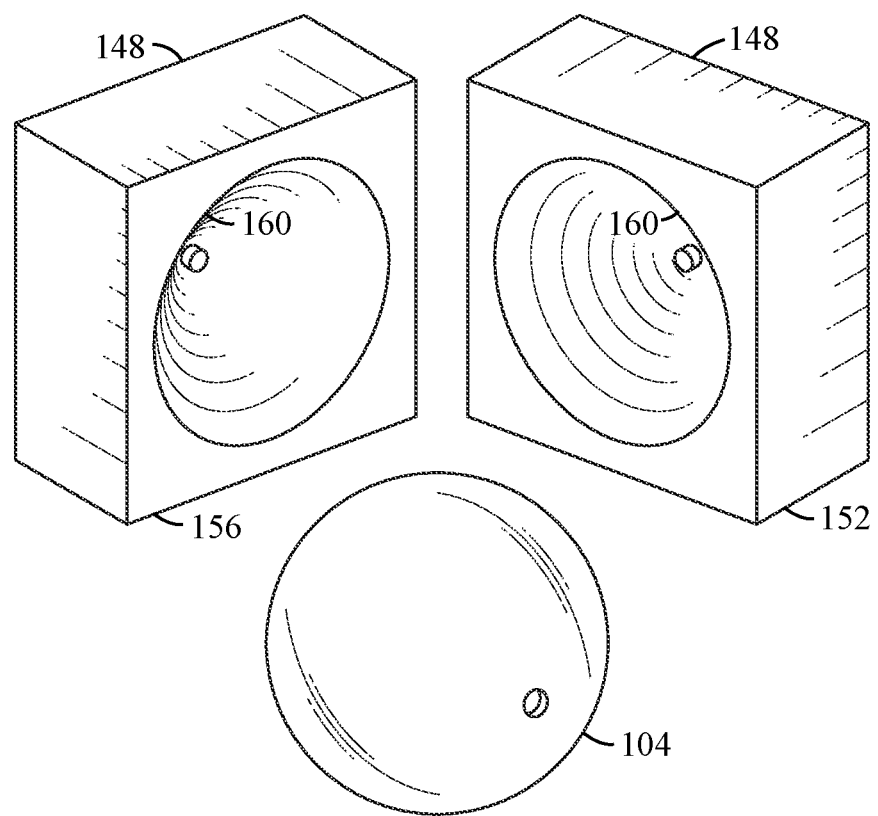
FIG. 6 illustrates a perspective view of the mold and frozen serum, according to some embodiments.

FIG. 6 illustrates a perspective view of the mold 148 and frozen serum 104 separated therefrom. The mold 148 includes an opening to permit the mold to be at least partially filled with the serum composition prior to freezing the serum composition. The opening may include a cap to allow the user to dispense the serum therein prior to freezing. The cap may also relieve pressure within the reservoir if overfilled with serum. The mold 148 may include a half 152 separable from a second half 156 to allow the mold to open and the frozen serum 104 to be removed from the mold 148. During use, the first half 152 and second half 156 are placed together to form a reservoir 160 wherein the serum composition is disposed and the frozen serum is formed. The reservoir 160 is able to be filled with and retain a skin care product that is a liquid or semi-liquid at standard atmospheric pressure and temperature, and that freezes at lower temperatures. Many types of personal care products will freeze at temperatures substantially close to 0° C., but those that freeze at higher or lower temperatures may also be useful. The reservoir 160 should be able to withstand serum expansion and contraction without rupturing. It should also be non-reactive with the products that it is intended to hold. In such, reservoir may be fashioned out of elastic materials, such as thermoplastic elastomers or silicone rubbers.

In some embodiments, the frozen serum 104 may be used without the applicator 100. In such that user simply holds the frozen serum 104 in their hand and applies the frozen serum onto their skin.

In some embodiments, once the frozen serum 104 has been applied to the skin, the frozen serum may be melted and redisposed with additional serum into the mold.

In some embodiments, the mold may be pre-filled at the time of manufacture, and/or may be refilled by the user. When the mold is filled at the factory, the reservoir will be filled by any means known in the field of personal care products, such as being dispensed under pressure through a filling nozzle. Whether the mold is sold filled or empty, a supply of serum will be separately provided so that the consumer can fill the mold as needed. The separately supplied product is a liquid and can be dispensed into the mold from a container in which the serum is provided. Typically, the serum to be filled will be in a liquid state, at a temperature above the freezing point of the product.

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

It will be appreciated by persons skilled in the art that the present embodiment is not limited to what has been particularly shown and described hereinabove. A variety of modifications and variations are possible in light of the above teachings without departing from the following claims.

What is claimed is:

1. A frozen serum and applicator thereof, comprising:
a mold having a first half releasably engaged with a second half, when engaged, the first half and the second half forming a reservoir therebetween to accept a volume of the serum, wherein the serum is frozen within the mold; and
the frozen serum having at least one receiver molded thereon, the receiver to releasably engage with the applicator,
wherein the applicator includes a handle portion positioned at a first end of the applicator and a receiver portion positioned at a second end of the applicator and comprising a first flexible arm and a second flexible arm, and wherein the first flexible arm and the second flexible arm comprise a protrusion to interface with the at least one receiver on the frozen serum to permit the frozen serum to be rolled.

2. A frozen serum and applicator thereof, comprising:
a mold having a first half releasably engaged with a second half, when engaged, the first half and the second half forming a reservoir therebetween to accept a volume of the serum, wherein the serum is frozen within the mold to produce the frozen serum having at least one receiver molded thereon, the receiver to releasable engage with the applicator configured to permit the frozen serum to be rolled; and
an opening to permit the serum to be disposed within the reservoir.

3. The frozen serum and applicator of claim 2, wherein the serum is comprised of at least one of the following: hyaluronic acid, vitamin C, jojoba oil, aloe vera, and retino.

4. The frozen serum and the applicator of claim 3, wherein the serum has a freezing temperature of 0° Celsius.

5. The frozen serum and applicator of claim 4, wherein the applicator includes a handle portion positioned at a first end of the applicator.

6. The frozen serum and applicator of claim 5, wherein the applicator includes a receiver portion positioned at the second end of the applicator.

7. The frozen serum and applicator of claim 6, wherein the receiver portion includes a first arm and a second arm.

8. The frozen serum and applicator of claim 7, wherein the first arm and the second arm each include a protrusion to interface with the at least one receiver on the frozen serum to permit the frozen serum to be rolled.

9. The frozen serum and applicator of claim 8, wherein the first arm and the second arm are flexible.

10. The frozen serum and applicator of claim 9, wherein the frozen serum is shaped as a sphere.

11. The frozen serum and applicator of claim 9, wherein the frozen serum is shaped as a cylinder.

12. The frozen serum and applicator of claim 11, wherein the handle portion releasably engages with the receiver portion.

13. The frozen serum and applicator of claim 12, wherein the frozen serum is melted and reused.

14. A frozen serum and applicator thereof, comprising:
- a mold having a first half releasably engaged with a second half, when engaged, the first half and the second half forming a reservoir therebetween to accept a volume of the serum, wherein the serum is frozen within the mold to produce the frozen serum having at least one receiver molded thereon, the receiver to releasable engage with the applicator configured to permit the frozen serum to be rolled onto the skin of a user;
- an opening to permit the serum to be disposed within the reservoir and frozen therein; and
- the applicator including a handle portion and a receiver portion, the receiver portion including a first arm and a second arm to retain the frozen serum thereon.

15. The frozen serum and applicator of claim 14, wherein the serum is comprised of at least one of the following: hyaluronic acid, vitamin C, jojoba oil, aloe vera, and retino.

* * * * *